United States Patent
Sato

Patent Number: 5,457,725
Date of Patent: Oct. 10, 1995

[54] ANALYZING METHOD FOR FOREIGN MATTER STATES

[75] Inventor: Masao Sato, Tokyo, Japan

[73] Assignee: Seiko Instruments Inc., Tokyo, Japan

[21] Appl. No.: 220,598

[22] Filed: Mar. 31, 1994

[30] Foreign Application Priority Data

Mar. 31, 1993 [JP] Japan ........................... 5-74855

[51] Int. Cl.[6] ................................... G01N 23/223
[52] U.S. Cl. .................. 378/44; 378/46; 378/45; 378/53
[58] Field of Search .................. 378/44, 45, 46, 378/50, 53, 54, 55, 86, 88, 89

[56] References Cited

U.S. PATENT DOCUMENTS 5,081,658  1/1992  Imai et al. .................. 378/44

Primary Examiner—David P. Porta
Assistant Examiner—Don Wong
Attorney, Agent, or Firm—Spensley Horn Jubas & Lubitz

[57] ABSTRACT

A method for identifying foreign matter in or on a sample, using apparatus composed of an X-ray generator, an X-ray detector, and a sample stage having a tilting mechanism capable of fixing a sample and changing both its irradiation and detection angles at the same time, an inclination fixing jig, and a calculation processing unit for executing bulk composition calculation at each angle according to the obtained X-ray intensity which is detected at the each angle. A judgment is made such that there is foreign matter mixed in the sample material when the bulk composition indications are coincident even when the angle is changed, while there is foreign matter at the surface of the sample when the bulk composition indications are not coincident.

3 Claims, 2 Drawing Sheets

ANALYZING METHOD FOR FOREIGN MATTER STATES

BACKGROUND OF THE INVENTION

The present invention relates to an analyzing apparatus for surface foreign matter states which determines and analyzes whether foreign matter is contaminated in a material itself, or adheres to a surface due to abrasion and consumption of parts of line constitution elements, solutions and oil in foreign matter analysis in schedule control.

In the prior art, generally known examination methods have utilized a secondary ionization mass spectrometry method (SIMS) in which analysis in the depth direction is performed by mass spectrometric analysis of secondary ions released from a sample by irradiating ions onto a sample surface, an electron beam probe X-ray microanalyzer (EPMA, XMA) combined with sputtering and etching methods, and a depth analyzing method using a surface analyzing apparatus such as an Auger electron spectrometric method (AES).

SIMS has excellent detection sensitivity as compared with other surface analyzing methods and is capable of macromolecular analysis and insulation material analysis, so that it is utilized as a depth analysis method in a variety of micro fields.

EPMA utilizes an electron beam having a diameter of not more than 1 micron and can obtain a great deal of information such as reflected electrons and secondary electrons other than characteristic X-ray beams, so that it is also utilized in quality control as an examination apparatus in a variety of fields not only for fundamental research analysis but also for purposes from pollution analysis to image observation and analysis of states with respect to non-destructive micro regions on surfaces.

In the prior art, the above-mentioned analyzing apparatuses are utilized for the purpose of surface foreign matter examination. However, as a means for selecting the area to be examined, human eyes or a microscope of a low magnification (about several hundred-power) is used, a recognition size of which is about more or less 50 microns in many cases.

The reason why this purpose has been responded to by means of an electron beam of not more than 1 micron and an ion beam results from the fact that there has been no probe having a suitable size. In the case of an apparatus in which the electron beam or the ion beam is utilized as the probe, it is necessary for its irradiating system to be held at high vacuum (about $10^{-4}$ Pa), in which operation and maintenance are extremely complicated, and the apparatus itself has been extremely expensive.

In addition, in any case, a destructive analyzing method utilizing sputtering is consequently provided, while when the purpose is surface examination for a product, non-destructive analysis is desired in many cases, and there has been no suitable method of this type.

SUMMARY OF THE INVENTION

An object of the present invention is to provide a non-destructive method in which foreign matter state analysis can be performed in an easy manner.

In order to achieve the above and other objects, the invention provides a fluorescent X-ray analyzing apparatus for observation of foreign matter in or on a sample, the apparatus including an X-ray exciting source such as an X-ray generator for irradiating the sample, an optical microscope mechanism for ensuring an irradiation position of a collimated primary X-ray beam, an X-ray detector for detecting a fluorescent X-ray beam generated from the sample, a sample stage having a tilting mechanism capable of fixing the sample at two angles including a horizontal position and one more inclined positions, and a calculation processing unit capable of performing bulk composition calculation or film thickness and composition calculation for thin films according to the intensity of the detected fluorescent X-ray beam, wherein compositions calculated by using the two angles as calculation factors are compared for each angle.

By the constitution as described above, with respect to the fluorescent X-ray analyzing apparatus constituted by a calculation processing unit which can perform bulk composition calculation according to the intensity of the detected fluorescent X-ray beam, a determination is made. It is concluded that material-contaminated foreign matter exists when the compositions compared for each angle are coincident, and that there is a surface-adhering foreign matter when they are not coincident. With respect to the fluorescent X-ray analyzing apparatus constituted by a calculation processing unit which can perform film thickness and composition calculation for thin films according to the intensity of the detected fluorescent X-ray beam, judgment can be made such that there is surface-adhering foreign matter when the compositions are coincident, while there is material-contaminated foreign matter when they are not coincident.

DESCRIPTION OF THE PREFERRED EMBODIMENTS

Figure 1:
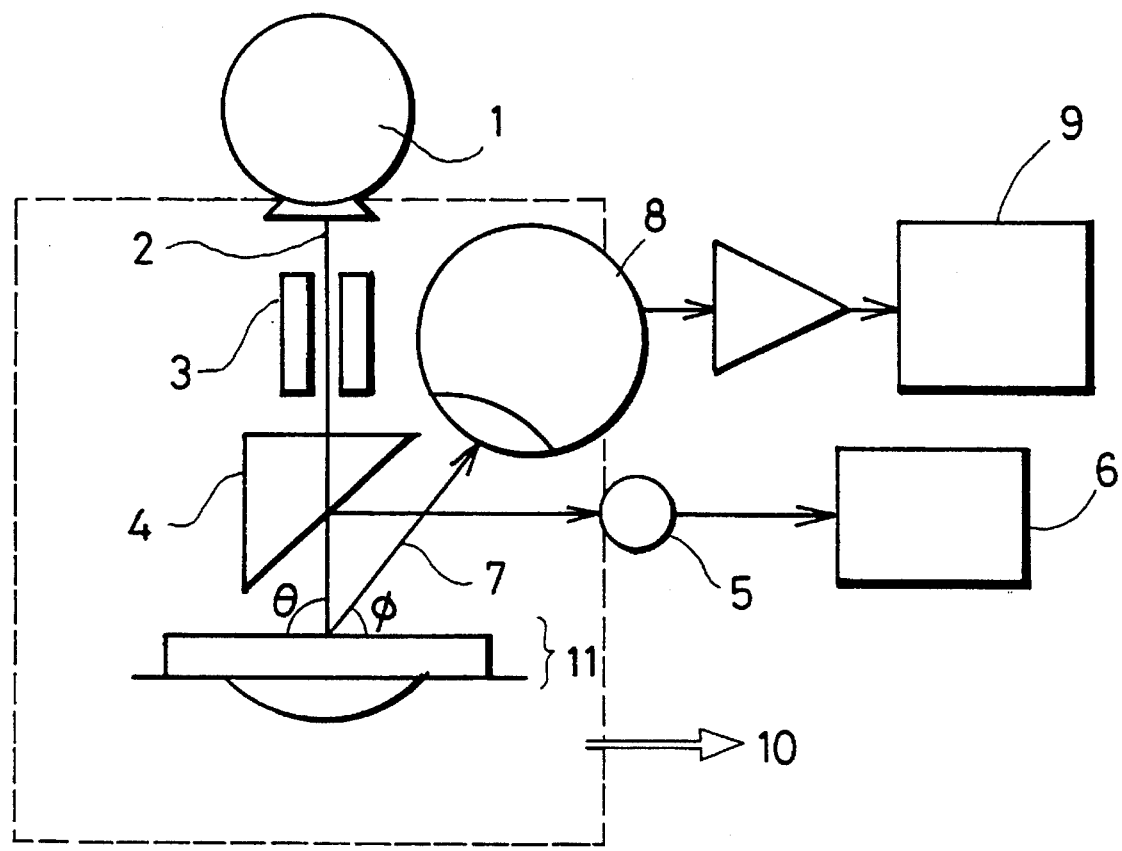
FIG. 1 is a simplified pictorial view of a system for implementing the present invention.

An embodiment of the present invention will be described hereinafter. Referring to FIG. 1 image observation can be performed on a sample set on a sample stage 11 using a semi-reflecting mirror 4, a CCD optical system 5 having a magnification switching mechanism, and a television monitor 6, so as to detect foreign matter, and positional determination is effected in accordance with an irradiation position of a primary X-ray beam 2 emitted from an X-ray generator 1.

Next, the start of measurement is initiated by an operation controller unit 9, whereby the primary X-ray beam 2 is collimated and directed by a collimator 3 and irradiated onto the sample. A fluorescent X-ray beam 7 excited by the sample is detected by an X-ray detector 8, the output of detector 8 is processed in the operation controller unit 9 including an X-ray counting circuit, and information capable of identifying elements, that is an X-ray spectrum, is obtained. A vacuum exhaust system 10 must be utilized when light elements such as sodium and the like, namely those having low X-ray energy, are to be detected. The sample stage 11 has a mechanism for horizontal positioning during a first measurement and for tilting during a second measurement.

The first measurement is executed using an irradiation angle $\Theta$ of 90 degrees with respect to the sample and a detection angle $\phi$ of 60 degrees. In the second measurement, the sample is tilted by 45 degrees with respect to the irradiation-detection angles, so as to obtain an irradiation angle Θ of 45 degrees and a detection angle φ of 105 degrees. When the sample stage 11 has no tilting mechanism, it is also possible that the first measurement is performed with sample stage 11 in the horizontal position shown in FIG. 1, and the second measurement is performed with the sample on a jig providing using a support surface inclined at 45 degrees to the horizontal.

Figure 2:
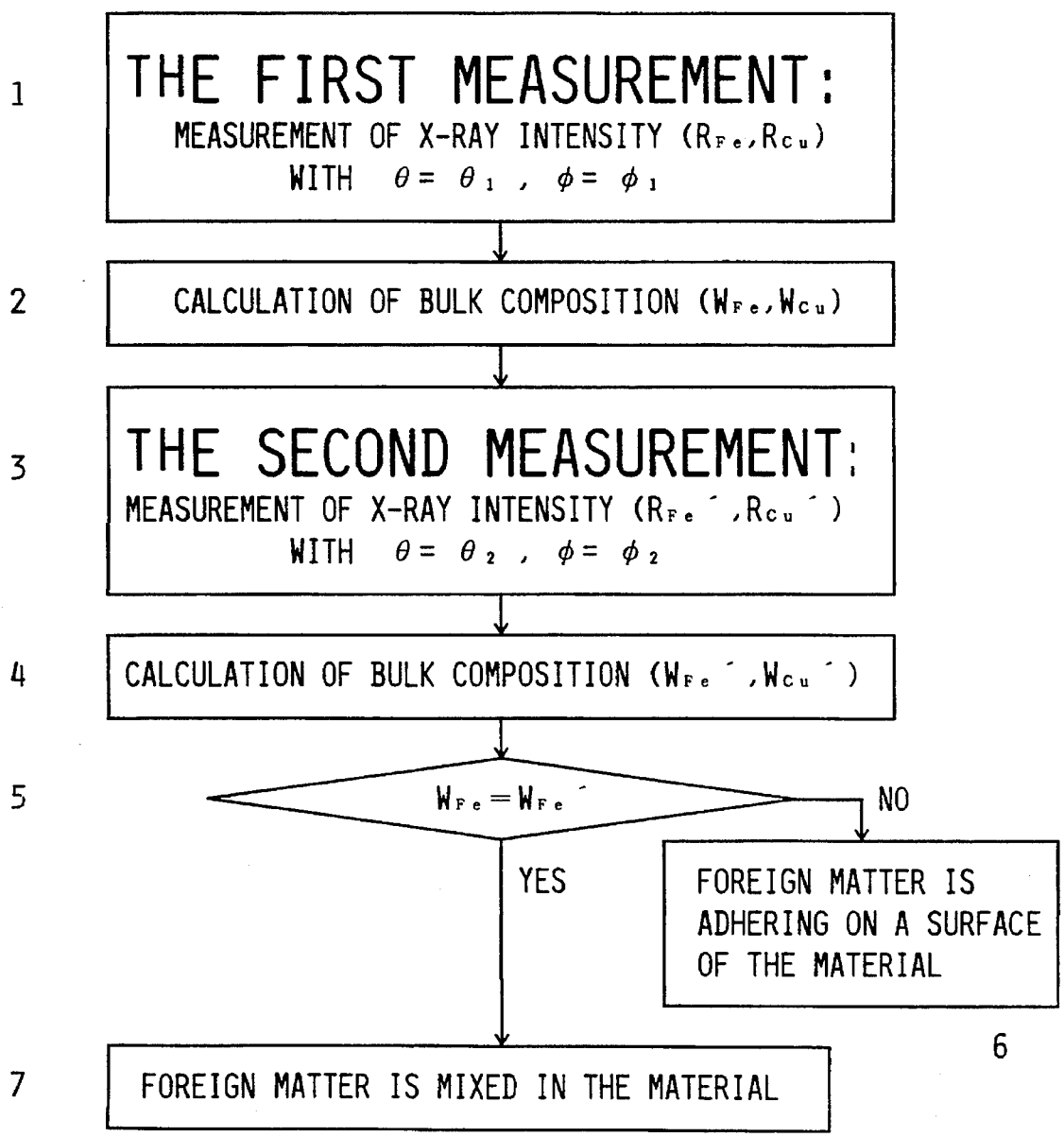
FIG. 2 is a process flow chart of foreign matter state analysis according to the present invention.

When Fe is detected as a foreign substance for a Cu material, a judgment algorithm for whether this Fe is mixed into the material or is a surface-adhering foreign substance is performed as depicted by the flow chart shown in FIG. 2.

In the first measurement, namely with an incident angle $\Theta=\Theta_1=90°$ and an outgoing angle $\phi=\phi_1=60°$, an X-ray intensity $I_{Fe}$ of iron (Fe) and an X-ray intensity $I_{Cu}$ of copper (Cu) are detected. Provided that an intensity R, in which the X-ray intensity obtained herein is standardized using an infinite thickness intensity, that is an X-ray intensity of a pure substance in which the X-ray intensity is saturated, is provided in an X-ray optical system as $R_{Fe}=0.0184$ and $R_{Cu}=0.976$ respectively, when bulk composition calculation is performed by means of a fundamental parameter (FP) method, an Fe composition of 1 wt % is determined. If this X-ray of Fe originates from an Fe film on copper, this X-ray intensity corresponds to 717 Angstroms with this X-ray optical system. Next, when a bulk composition is calculated from the second measurement, namely using X-ray intensities $R_{Fe}'$, $R_{Cu}'$ obtained at an incident angle $\Theta=\Theta_2=45°$ and an outgoing angle $\phi=\phi_2=105°$, if an Fe composition of 1 wt % is determined, the assumption in the bulk calculation is correct, and it can be judged that this foreign matter Fe is a foreign substance mixed in a copper material.

If a result of the composition calculation in the second measurement is not more than 1 wt % and is a value different from the result in the first measurement, it can be concluded that the assumption in the bulk calculation is incorrect, and it can be judged that this foreign matter Fe is surface-adhering foreign matter which adheres on the surface of the copper material. In the case of electron beam excitation, the bulk calculation is executed by a ZAF method, and a determination is made in the same manner. When the film thickness and the composition are determined according to a thin film FP method, a reverse determination to the above is executed according to the composition.

According to the present invention, when foreign matter analysis must be quickly executed due to a claimed sample and the like in the course of quality control, or when foreign matter state analysis must be performed for determining whether a material is contaminated with foreign matter or whether the foreign matter adheres to a surface in the course of schedule control, it becomes possible to perform processing rapidly in a non-destructive manner, and further in the case of the X-ray excitation method, no high vacuum is required, so that the apparatus can also be made structurally simple, and it is possible to provide an expensive apparatus in which operation and maintenance are easy.

This application relates to subject matter disclosed in Japanese Application number 5-74855, filed on Mar. 31, 1993, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A fluorescent X-ray analyzing method for determining foreign matter states using a fluorescent X-ray analyzing apparatus constituted by an optical microscope mechanism for observing foreign matter on or in a sample irradiated by an X-ray exciting source and establishing an irradiation position of a primary X-ray beam by collimating an X-ray beam from the X-ray exciting source, an X-ray detector for detecting a fluorescent X-ray beam emitted from the sample in response to irradiation by the primary X-ray beam, a sample stage having means for selectively fixing the sample at each of two different angular positions including a horizontal position and an angular position which is inclined to the horizontal, and a calculation processing unit for executing bulk composition calculations or film thickness and composition calculations for thin films based on the intensity of the fluorescent X-ray beam detected by the X-ray detector, said method comprising: irradiating the sample with the primary X-ray beam and detecting fluorescent X-rays emitted from the sample while the sample is in each of the angular positions; executing calculations by the calculation processing unit; and comparing the calculation results associated with the two angular positions of the sample for determining whether foreign matter is adhering to the surface of the sample or is mixed into the material of the sample.

2. An electron beam-exciting X-ray analyzing method for determining foreign matter states using an electron beam-exciting X-ray analyzing apparatus constituted by an optical microscope mechanism for observing foreign matter on or in a sample irradiated by an X-ray exciting source and establishing an irradiation position of the electron beam, an X-ray detector for detecting an X-ray beam emitted from the sample in response to radiation from the X-ray exciting source, a sample stage having a tilting mechanism for selectively fixing the sample at each of two different angular positions including a horizontal position and an angular position which is inclined to the horizontal, and a calculation processing unit for executing bulk composition calculations based on the intensity of the detected X-ray beam, said method comprising: irradiating the sample with the X-ray beam from the X-ray exciting source and detecting the X-ray beam emitted from the sample while the sample is in each of the angular positions; executing calculations by the calculation processing unit; and comparing the calculation results associated with the two angular positions of the sample for indicating that: foreign matter is mixed into the material of the sample when the calculation results indicate identical compositions for calculations associated with the two angular positions; and foreign matter is adhering to the surface of the sample when the calculation results indicate dissimilar compositions for calculations associated with the two angular positions.

3. An electron beam-exciting X-ray analyzing method for determining foreign matter states using an electron beam-exciting X-ray analyzing apparatus constituted by a mechanism irradiated by an electron beam for obtaining an electron beam scanning image, an X-ray detector for detecting an X-ray beam emitted from a sample in response to irradiation by the electron beam, a sample stage having a tilting mechanism for selectively fixing the sample at each of two different angular positions including a horizontal position and an angular position which is inclined to the horizontal, and a calculation processing unit for executing bulk composition calculations based on the intensity of the detected X-ray beam, said method comprising: irradiating the sample with the electron beam and detecting the X-ray beam emitted from the sample while the sample is in each of the angular positions; executing calculations by the calculation processing unit; and comparing the calculation results associated with the two angular positions of the sample for indicating that: foreign matter is mixed into the material of the sample when the calculation results indicate identical compositions for calculations associated with the two angular positions; and foreign matter is adhering to the surface of the sample when the calculation results indicate dissimilar compositions for calculations associated with the two angular positions.

* * * * *